(12) United States Patent
Sipka et al.

(10) Patent No.: US 8,333,976 B2
(45) Date of Patent: Dec. 18, 2012

(54) PROCESSES FOR INHIBITING DEVELOPMENT OF ALLERGIC DISEASE

(76) Inventors: Sandor Sipka, Debrecen (HU); Lorand Bertók, Budapest (HU); Geza Bruckner, Versailles, KY (US); Schnitzer Ferenc, Gödöllö (HU)

(*) Notice: Subject to any disclaimer, the term of this patent is extended or adjusted under 35 U.S.C. 154(b) by 1097 days.

(21) Appl. No.: 10/651,136

(22) Filed: Aug. 28, 2003

(65) Prior Publication Data
US 2005/0048085 A1 Mar. 3, 2005

(51) Int. Cl.
A61K 38/00 (2006.01)
A61K 39/02 (2006.01)
A61P 31/00 (2006.01)

(52) U.S. Cl. ...................... 424/234.1; 514/2.1
(58) Field of Classification Search .................. None
See application file for complete search history.

(56) References Cited

U.S. PATENT DOCUMENTS
6,440,426 B1 8/2002 Wheeler et al.

OTHER PUBLICATIONS

Tulic et al., AM.J. Resp. Cell. Mol. Biol. vol. 22, pp. 604-612, 2000.*
Liu et al., Current Reviews of Allergy and Clinical Immunology, vol. 109, pp. 379-392, 2002.*
Lin et al. "The association between lung innate immunity and differential airway antigen-specific immune responses." In. Immunol. 8(4): 499-507, 1996.*
Avian Health Network Newsletter, vol. II, Issue XI, Aug. 2004. http://www.stoppdd.org/happenings/newsletter_work/04_08_news.html.*
Lillehoj et al. 'Recent Progress on the Cytokine Regulation of Intestinal Immune Responses to *Eimeria*.' Poultry Science 83:611-623, 2004.*
Lillehoj et al. 'Host immunity and Vaccine Development to Coccidia and *Salmonella* Infections in Chickens.' J. Poultry Science 40:151-193, 2003.*
Bischoff et al. 'Role of mast cells in allergic and non-allergic immune responses: comparison of humand murine data.' Nature Rev. 7:93-104, 2007.*
Kurucz et al. 'Current Animal Models of Bronchial Asthma.' Curr. Pharm. Des. 12:3175-3194, 2006.*
Malling et al. 'Bacterial vaccines: anything but placebo.' Allergy. 55:214-218, 2000.*
Previte et al. 'Detoxification of *Salmonella typhimurium* lipopolysaccharide by ionizing radiation.' J. Bacteriol. 93(5):1607-1614, 1967.*
Tarpley et al. 'Radiation Sterilization' J. Bacteriol. 65(3):305-309, 1953.*
Shultz et al. 'Radiation degradation of polymethacrylates. Dose rate and medium effects.' J. Polymer. Science. Part A 1:1651-1669, 1963.*
Gereda et al. Relation between house dust endotoxin exposure, type 1 T-cell development, an allergen sensitization in infants at high risk of asthma. lancet 355:1680-1683, 2000.*

Oehling et al. 'Bacterial immunotherapy of childhood bronchial asthma.' Allergol. et Immunopathol. VIII:177-184, 1980.*
Cochran et al. 'Influence of Lipopolysaccharide Exposure on Airway Function and Allergic Responses in Developing Mice.' Pediatric Pulmonology. 34:267-277, 2002.*
Khan et al. 'Functional and immune response to lipopolysaccharide and allergens in developing mice.' Pediatr. Res. 51: 474A, 2002.*
Baldridge et al. 'Monophosphoryl lipid A enhances mucosal and systemic immunity to vaccine antigens following intranasal administration.' Vaccine 18:2416-2425, 2000.*
Lauw et al, "Reduced Th1, but Not Th2, Cytokine Production by Lymphocytes after In Vivo Exposure of Healthy Subjects to Endotoxin", *Infection and Immunity*, Mar. 2000, pp. 1014-1018.
Salkowski et al, "Lipopolysaccharide and Monophosphoryl Lipid A Differentially Regulate Interleukin-12, Gamma Interferon, and Interleukin-10 mRNA Production in Murine Macorphages," *Infection and Immunity*, Aug. 1997, pp. 3239-3247.
Henricson et al, "Differential Cytokine Induction by Doses of Lipopolysaccharide and Monophosphoryl Lipid A That Result in Equivalent Early Endotoxin Tolerance", *Infection and Immunity*, Aug. 1990, pp. 2429-2437.
Holt et al, "Microbial stimulation as an aetiologic factor in atopic disease", *Allergy*, 1999, 54, pp. 12-16.
Sabina Illi et al, "The pattern of atopic sensitization is associated with the development of asthma in childhood", *The Journal of Allergy and Clinical Immunology*, Nov. 2001, part 1, vol. 108, No. 5.
L. Bertók, "Radio-detoxified Endotoxin, a Potent Stimulator of Non-specific Host Defence", *Advances in the Biosciences*, vol. 68, pp. 365-371, 1988 Pergamon Journals Ltd.
Gyorgy Fust, et al, "Interactions of Radio-Detoxified *Escherichia coli* Endotoxin Preparations with the Complement System", *Infection and Immunity*, vol. 16, No. 1, pp. 26-31, 1977.
Weiss, Scott T., M.D., "Eat Dirt—The Hygiene Hypothesis and Allergic Diseases", *The New England Journal of Medicine*, vol. 347, No. 12, Sep. 19, 2002, pp. 930-931.
E. von Mutius et al, "Is asthma linked to atopy?", *Clinical and Experimental Allergy*, vol. 31, pp. 1651-1652, 2001.
Dr. Nádházi Zoltán et al, "Egészséges véradók plazma endotoxin szintje", Orvosi Hetilap, 139 (48), pp. 2889-2891, Nov. 29, 1998.
I. Barna et al, "Radiodetoxified Lipopolysaccharide Fails to Activate the Hypophyseal-Pituitary-Adrenal Axis in the Rat", NeuroImmunoModulation, 2000;8:pp. 128-131.
Charlotte Braun-Fahrländer et al, "Environmental Exposure to Endotoxin and Its Relation to Asthma in School-Age Children", *The New England Journal of Medicine*, vol. 347, Sep. 19, 2002, No. 12, pp. 869-877.
Wasim Maziak et al, "Asthma and farming", *The Lancet*, vol. 359, Feb. 16, 2002, pp. 623-624.
Josef Riedler et al, "Exposure to farming in early life and development of asthma and allergy: a cross-sectional survey", *The Lancet*, vol. 358, Oct. 6, 2001, pp. 1129-1133.
Tamara Kubasova et al, "Modifying Effects of the Parent and Radio-Detoxified Endotoxins on Cell-Mediated Cytotoxicity and Cytokine Release", *Acta Microbiologica Hungarica*, 40(3), pp. 249-254 (1993).
E. Gilad et al, "Effects of radiodetoxified endotoxin on nitric oxide production in J774 macrophages and in endotoxin shock", *Journal of Endotoxin Research*, (1996) 3(6), pp. 513-519.

(Continued)

*Primary Examiner* — Nora Rooney
(74) *Attorney, Agent, or Firm* — Dinsmore & Shohl LLP

(57) ABSTRACT

A process for inhibiting development of allergic disease comprises exposing a neonatal or immature mammal or bird to irradiation-detoxified lipopolysaccharide derived from microbial, protozoan and/or fungal endotoxin.

19 Claims, No Drawings

OTHER PUBLICATIONS

L. Bertók, "Radiodetoxified Endotoxin-Induced Tolerance Effect on Endotoxin Lethality and Macrophage Arachidonic and Metabolism", *Acta Microbiologica et Immunologica Hungarica*, 42(4), pp. 409-417 (1995).

Lóránd Bertók, "Stimulation of Nonspecific Resistance by Radiation-Detoxified Endotoxin", *Beneficial Effects of Endoxtoxins*, Plenum Publishing Corp., 1983, pp. 213-226.

P.M. Matricardi et al, "Microbial products in allergy prevention and therapy", *Allergy*, 2003: 58:pp. 461-471.

Fernando D. Martinez et al, "Role of microbial burden in aetiology of allergy and asthma", *Paediatrics*, vol. 354, Sep. 1999, pp. sn12-sn15.

Pierre Ernst et al, "Relative Scarcity of Asthma and Atopy among Rural Adolescents Raised on a Farm", *Am. J. Respir. Car Med.*, vol. 161 pp. 1563-1566, 2000.

Jose E. Gereda, M.D. et al, "Levels of Environmental Endotoxin and Prevalence of Atopic Disease", *JAMA*, Oct. 4, 2000, vol. 284, No. 13, pp. 1652-1653.

Erzsébet Elekes et al, "Alterations in the Chemical Composition and Antigenicity of *Escherichia coli* 089 Lipopolysaccharide and Lipid A After $^{60}CO$ Gamma Irradiation", *Acta Microbiologica Hungarica*, 35 (3), pp. 301-305 (1988).

G.E.L. Walraven et al, "Asthma, smoking and chronic cough in rural and urban adult communities in The Gambia", *Clinical and Experimental Allergy*, 2001, vol. 31, pp. 1679-1685.

Ulrike Gehring et al, "House Dust Endotoxin and Allergic Sensitization in Children", *Am J Respir Crit Care Med*, vol. 166, pp. 939-944, 2002.

Thorn, J., "The inflammatory response in humans after inhalation of bacterial endotoxin: a review", *Inflamm. Res.* 50 (2001) 254-261.

Lóránd Bertók, "Prevention of Cardiac Damage Induced by Formyl-Leurosine, a Potent Cytostatic Agent, by Radio-Detoxified Endotoxin (Tolerin®) in Dogs", *Immunopharmacology*, 8 (1984) 13-17.

L. Bertók, "Stimulation of Nonspecific Resistance by Radio-Detoxified Endotoxin", *Endotoxin*, Plenum Publishing Corp., 1990, pp. 13-17.

L. Bertók, "Stimulation of Nonspecific Resistance by Radio-Detoxified Endotoxin", *Endotoxin*, Friedman et al, Editors, Plenum Publishing Corp., 1990, pp. 677-679.

* cited by examiner

PROCESSES FOR INHIBITING DEVELOPMENT OF ALLERGIC DISEASE

FIELD OF THE INVENTION

The present invention is directed to processes for inhibiting development of allergic disease, particularly in mammals and birds. More specifically, the invention is directed to processes for inhibiting development of allergic disease by treatment of a neonatal or immature mammal or bird.

BACKGROUND OF THE INVENTION

A major health issue in the western world is the increase in allergic (atopic) diseases, e.g. asthma and allergies. It has been estimated that the incidence of asthma and allergies affects from about 15 to 30% of the population and continues to increase, with a major impact on health and productivity. Currently available remedies are typically primarily aimed at short-term treatment via antihistamines and topical nasal steroids. Preventive measures have generally not been very successful or well tolerated, e.g. allergy shots to common allergens. Accordingly, the need exists for additional preventive or inhibitive measures.

SUMMARY OF THE INVENTION

Accordingly, it is an object of the present invention to provide novel means for inhibiting allergy development. It is a further object to provide improved means for inhibiting allergy which overcome various disadvantages of prior art allergy treatments.

These and additional objects are provided by the present invention. In one embodiment, the invention is directed to a process for inhibiting development of allergic disease. The process comprises exposing a neonatal or immature mammal or bird to irradiation-detoxified lipopolysaccharide derived from microbial, protozoan and/or fungal endotoxin.

Additional embodiments of the invention are described in further detail below. The present inventors have discovered that safe application of lipopolysaccharide (LPS) into the natural environment for young children or animals, currently living in an "overly sterilized" environment, helps to restore the development of normal immune functions and inhibits the development of allergies later in life. Additional objects, embodiments and advantages of the invention will be more fully apparent and understood in view of the following detailed description.

DETAILED DESCRIPTION

The present invention is directed to processes for inhibiting development of allergic disease. The processes comprise exposing a neonatal or immature mammal or bird to irradiation-detoxified lipopolysaccharide derived from microbial, protozoan and/or fungal endotoxin. Within the context of the present specification, the term "inhibiting" encompasses both decreasing the development and, in certain embodiments, preventing the development, of allergy. Additionally, within the context of the present specification, the term "immature" refers to a mammal or bird which has not completed life cycle development to its adult stage. Further, within the context of the present specification, the term "allergic disease" encompasses allergic atopic disease, e.g., both allergies and asthma.

It has been recently reported that growing up on a farm versus the modern urban "sterile" environment protects against allergic sensitization as well as the development of childhood allergic disease. See, for example, Ernst, P. et al, Am J Resp Crit Care Med, 161: 1563-1566 (2000), Gereda, J. E. et al, JAMA, 284: 1652-1653 (2000), and Gehring, U. et al, Am J Respir Crit Care Med, 166:939-944 (2002). It appears that regular contact with farm animals confers a protective effect. The protective effect of this environment has been linked to increased concentrations of endotoxin from gram-negative bacteria, which seem to stimulate the immune system. See, for example, Braun-Fahrlander, C. et al, N Engl J Med, 347:869-877 (2002) and Martinez, F. D., et al, Lancet, 354 suppl 2: SII 12-15 (1999). A microbial burden has been suggested to be crucial during the first years of life for developing a non-atopic, protective immune response, Matricardi, P. M., et al, Allergy, 58: 461-471 (2003). The cell components from bacteria, which are primarily responsible for activating the immune response are the lipopolysaccharides (LPS). However, LPS have undesirable side effects such as pyrogenicity, hypotension, and the like which typically prevent or at least limit their use as an immune stimulant, Thorn, J., Inflamm. Res., 50: 254-261 (2001). Füst et al., Infect Immun., 16: 26-31 (1977) have demonstrated that irradiation of LPS decreases their toxicity. Bertók et al. found that detoxified LPS retain some of their beneficial properties in animal experiments, Immunopharmacology, 8: 13-17 (1984), and, furthermore, irradiated LPS are not toxic as tested in human volunteers, Orvosi Hetilap, 140: 819-827 (1999).

The present inventors have now determined that irradiated LPS, versus native LPS, have significantly less stimulatory effect on Il-1 production of the cells in peripheral heparinized blood, as set forth in Table 1.

TABLE 1

In vitro comparison of the interleukin 1 (IL-1) released by native endotoxin (LPS) and irradiation-detoxified LPS (RDTX-LPS) from heparinized human peripheral blood cells.

| CELLS | IL-1 (pg/ml) released (mean + SD) |
|---|---|
| Non-stimulated (control) cells | 9.12 + 8.6 |
| Cells stimulated with native LPS | 172.26 + 26.7 |
| Cells stimulated with RDTX-LPS | 98.22 + 19.4 |

(Average values of 3 experiments. Measurement of IL-1 by ELISA in the supernatants). It should be noted that the values of SD for native LPS stimulated cells compared to SD values for RDTX-LPS stimulated cells are different for $p<0.001$.

Accordingly, it is advantageous to inactivate the detrimental components of LPS derived from microbial (including bacterial), protozoan or fungal sources from a farm or other natural origin and then to apply the detoxified LPS fraction for stimulation of the Th-1 arm of the immune system. The safe application of LPS into the environment for young children or animals, for example, mammals or birds, currently living in an "overly sterilized" environment, will help to restore the development of normal immune function and prevent or decrease the development of allergies later in life.

In a more specific embodiment, the present processes provide a safe, irradiation detoxified LPS to young mammals in order to stimulate an immune response by stimulating the Th-1 arm of the immune system, thereby inhibiting, by preventing or minimizing, the development of allergic (atopic) disease such as common allergies and asthma. More specifically, the present process through irradiation inactivates the undesirable effects of the endotoxins from microbes, including bacteria, protozoan or fungi and while retaining their immune stimulatory antiallergenic properties. In one embodiment, the endotoxins are extracted from bacteria, protozoan or fungi. In a more specific embodiment, the endotoxins are extracted from bacterial, protozoan or fungal sources in a farming or other natural environment. In a further embodiment, the endotoxins are extracted from, for example, *E. coli*.

Any suitable extraction method known in the art may be employed, an example of which is a solvent extract system, preferably with polarity adjustment to maximize yield. Such solvent extraction systems may employ a phenol-water system, other alcohol-water systems, an acetonitrile-water system, or the like. The extracted endotoxins may then be irradiated with sufficient radiation to detoxify the toxins therein, for example radiation in an amount of from about 25 to about 150 kGy. The irradiation changes the structure of the endotoxin, removing toxicity, while maintaining its positive immune effect. Typically, the endotoxins may be irradiated in an aqueous solution. The neonatal or immature mammal or bird is exposed to the resulting detoxified LPS, whether through environmental exposure or by direct contact with the animal. As detailed below, exposure can be effected by various means, inducing the long-lasting stimulation of the immune system without any dangerous side-effects.

In one embodiment, the subject is an infant human. In a further embodiment, the subject is a human of 1 month to 2 years of age. In an alternate embodiment, the subject is a primate of 2 weeks to 12 months of age. In yet further embodiments, the subject is a dog or cat of 1 week to 12 months of age. In additional embodiments, the subject is a farm animal, for example a cow, pig, goat, horse, chicken or turkey of 2 days to 12 months of age.

The exposure may be achieved by various means. In one embodiment, a topical composition comprising the irradiation-detoxified lipopolysaccharide is applied to the subject. Any topical composition vehicle may be employed. For example, in one embodiment, the topical composition further comprises a powder vehicle or carrier, examples of which include, but are not limited to talcum powder, corn starch, beet starch, rice flour, oatmeal, or a mixture thereof. In an alternate embodiment, the topical composition is in the form of a topical cream, lotion or gel. Examples of suitable cream, lotion or gel base components include, but are not limited to, water, short and long chain alcohols, acids, esters and oils, alkylene glycols, glycerols, glycerides, petroleum jelly and the like. The compositions may also include additional components typically employed in topical compositions, for example, vitamins, fragrances, herbal extracts, humectants and the like.

The exposure may be achieved by contacting the subject with a cloth or film impregnated with, for example, a suspension or dispersion of the irradiation-detoxified lipopolysaccharide. Any type of woven or nonwoven natural or synthetic cloth may be employed. Suitably, the irradiation-detoxified lipopolysaccharide may be formulated in a water or water/alcohol base for impregnation. More specifically, the subject can be contacted with a wipe impregnated with a composition comprising the irradiation-detoxified lipopolysaccharide. In a further embodiment, an infant can be provided with a diaper impregnated with a composition comprising the irradiation-detoxified lipopolysaccharide.

Alternatively, the exposure may be achieved by administering an aerosol spray composition comprising the irradiation-detoxified lipopolysaccharide to surrounding environment or directly to the subject. Such a spray may contain an aqueous, organic or mixed vehicle and may be sprayed from a pressurized or manual pump spray container, in accordance with spray techniques known in the art. The aerosol spray may then be provided in a living area to achieve the desired exposure.

The exposure level should be that sufficient to obtain the desired inhibition effects. In a specific embodiment, the irradiation-detoxified lipopolysaccharide is delivered in a concentration from 0.01 ug/g to 100 ug/g of delivery vehicle, for example, topical composition, impregnated cloth, or aerosol spray. In a further embodiment, exposure to the irradiation-detoxified lipopolysaccharide is achieved shortly after birth and during the maturing life cycle of the mammal or bird. In a more specific embodiment, exposure to the irradiation-detoxified lipopolysaccharide is achieved on a daily or weekly basis during growth of the mammal or bird.

The following examples illustrate non-limiting specific embodiments of the compositions suitable for use in the processes of the invention.

EXAMPLE 1

This example demonstrates one embodiment for preparation of irradiated LPS. Other methods will be apparent to one of ordinary skill in the art and are equally suitable for use in connection with the present inventive processes.

From a fermented culture of *Escherichia coli* 0101 H, LPS is extracted by a modified "hot-phenol-water" method according to Westphal et al, *Z. Naturforsch.*, 76:148-155 (1952). The resulting powdered LPS is suspended in distilled water (10 mg/ml) and irradiated in the cabin of NORTOM equipment (with cooling) by $^{60}$Co gamma irradiation (150 kGy). The irradiated material is lyophilized immediately. The detoxification of LPS is measured using a biological test in animals for residual toxicity and for endotoxin tolerance inducing capacity. The irradiated LPS preparation can preserve its biological activity for about 10 years in the lyophilized form.

EXAMPLE 2

This example demonstrates a pressurized aerosol formulation:

| | |
|---|---|
| Sterile Water | 100 ml |
| Irradiated LPS | 10 ug/ml |

Butanol or Nitrogen (propellant) sufficient for aerosol delivery

EXAMPLE 3

This example demonstrates a manual pump aerosol formulation:

| | |
|---|---|
| Sterile Water | 100 ml |
| Irradiated LPS | 15 ug/ml |

EXAMPLE 4

This example demonstrates another manual pump aerosol formulation:

| | |
|---|---|
| 5% isopropyl alcohol | 100 ml |
| Irradiated LPS | 5 ug/ml |

EXAMPLE 5

This example demonstrates a dry powder formulation:

| | |
|---|---|
| Talcum powder | 100 grams |
| Dried irradiated LPS | 20 ug/gram talcum powder |

EXAMPLE 6

This example demonstrates another dry powder formulation:

| | |
|---|---|
| Corn starch | 100 grams |
| Dried irradiated LPS | 25 ug/gram corn starch |

EXAMPLE 7

This example demonstrates another dry powder formulation:

| | |
|---|---|
| Beet starch and rice flour | 100 grams |
| Dried irradiated LPS | 5 ug/gram beet starch |

EXAMPLE 8

This example demonstrates another dry powder formulation, particularly advantageous for application to a subject via bath water:

| | |
|---|---|
| Oatmeal | 100 grams |
| Dried irradiated LPS | 5 ug/gram oatmeal |

EXAMPLE 9

A cloth such as a diaper is provided with irradiated LPS applied uniformly as powder in an amount of about 0.01 ug. In another embodiment, a diaper is provided with irradiated LPS applied uniformly as a liquid in an aqueous carrier in an amount of about 0.01 ug.

In a further embodiment, a single wipe cloth is impregnated with irradiated LPS in an amount of about 0.01 ug/wipe.

EXAMPLE 10

This example demonstrates a topical cream or lotion formulation:

A base mixture of purified water, canola oil, stearic acid, glycerol stearate, propylene glycol, glycerin, cetyl alcohol, lecithin, aloe vera gel, squalane (vegetable), avocado oil, vitamins A, D and E, D-panthenol, allantoin, chamomile extract, herbal fragrance, propylparaben, methylparaben, and triethanolamine, is combined with irradiated LPS in an amount of about 10 ug irradiated LPS per 50 ml of the base mixture.

EXAMPLE 11

This example demonstrates another topical cream or lotion formulation:

| | |
|---|---|
| Petroleum jelly | 100 grams |
| Irradiated LPS | 0.1 ug/gram petroleum jelly |

EXAMPLE 12

This example demonstrates another topical cream or lotion formulation:

Base mixture of sweet almond oil, shea butter and vitamin E

| | |
|---|---|
| Irradiated LPS | 2.5 ug per gram base mixture |

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A process for decreasing development of allergic asthma, the process comprising exposing a neonatal or immature mammal to irradiation-detoxified lipopolysaccharide (IR-LPS) derived from extracted bacterial endotoxin and operable to stimulate the Th 1 arm of the mammal's immune system, wherein exposure comprises at least weekly administration during maturation of the mammal via application of the IR-LPS to a living environment of the mammal.

2. A process according to claim 1, wherein the irradiation-detoxified lipopolysaccharide is detoxified by exposure of the endotoxin to irradiation at a level of from about 25 to about 150 kGy.

3. A process according to claim 1, wherein the irradiation changes the structure of the endotoxin while maintaining its Th 1 stimulatory effect in the resulting irradiation-detoxified lipopolysaccharide.

4. A process according to claim 1, wherein an infant mammal is exposed.

5. A process according to claim 4, wherein the exposure is achieved by administering a topical composition comprising the irradiation-detoxified lipopolysaccharide to the infant mammal.

6. A process according to claim 5, wherein the topical composition further comprises a powder.

7. A process according to claim 6, wherein the powder comprises talcum powder, corn starch, beet starch, rice flour, oatmeal, or a mixture thereof.

8. A process according to claim 5, wherein the topical composition is in the form of a topical cream.

9. A process according to claim 1, wherein application is achieved by administering an aerosol spray composition comprising the irradiation-detoxified lipopolysaccharide.

10. A process according to claim 4, wherein the exposure is achieved by contacting the infant mammal with a wipe impregnated with a composition comprising the irradiation-detoxified lipopolysaccharide.

11. A process according to claim 4, wherein the exposure is achieved by contacting the infant mammal with a diaper impregnated with a composition comprising the irradiation-detoxified lipopolysaccharide.

12. A process according to claim 1, wherein the mammal is a human and during maturation is between 1 month and 2 years of age.

13. A process according to claim 1, wherein a primate of 2 weeks to 12 months of age is exposed.

14. A process according to claim 1, wherein a dog or cat of 1 week to 12 months of age is exposed.

15. A process according to claim 5, wherein the irradiation-detoxified lipopolysaccharide is delivered in a concentration from 0.01 ug/g to 100 ug/g of topical composition.

16. A process according to claim 1, wherein exposure to the irradiation-detoxified lipopolysaccharide is initiated shortly after birth and "during maturation" is throughout the maturing life cycle of the mammal.

17. A process according to claim 1, wherein administration is on a daily basis.

18. A process according to claim 1, wherein the mammal is a farm animal.

19. A process according to claim 18, wherein the farm animal is a cow, pig, goat, horse, chicken or turkey of 2 days to 12 months of age.

* * * * *

UNITED STATES PATENT AND TRADEMARK OFFICE
CERTIFICATE OF CORRECTION

PATENT NO. : 8,333,976 B2  
APPLICATION NO. : 10/651136  
DATED : December 18, 2012  
INVENTOR(S) : Sipka et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1209 days.

Signed and Sealed this
Eleventh Day of November, 2014

Michelle K. Lee
*Deputy Director of the United States Patent and Trademark Office*